(12) United States Patent
Hofstetter et al.

(10) Patent No.: US 11,660,440 B2
(45) Date of Patent: May 30, 2023

(54) WOUND CARE CONNECTION DEVICE AND WOUND CARE KIT

(71) Applicant: LOHMANN & RAUSCHER GMBH, Schoenau An der Triesting (AT)

(72) Inventors: Christoph Hofstetter, Vienna (AT); Arno Herzele, Brunn Am Gebirge (AT)

(73) Assignee: LOHMANN & RAUSCHER GMBH, Schoenau An der Triesting (AT)

( * ) Notice: Subject to any disclaimer, the term of this patent is extended or adjusted under 35 U.S.C. 154(b) by 894 days.

(21) Appl. No.: 16/564,182

(22) Filed: Sep. 9, 2019

(65) Prior Publication Data

US 2020/0001067 A1  Jan. 2, 2020

Related U.S. Application Data

(63) Continuation of application No. 15/211,172, filed on Jul. 15, 2016, now abandoned.

(30) Foreign Application Priority Data

Jul. 16, 2015  (EP) .................................... 15002121

(51) Int. Cl.
*A61M 5/30* (2006.01)
*A61M 39/10* (2006.01)
(Continued)

(52) U.S. Cl.
CPC ..... *A61M 39/105* (2013.01); *A61F 13/00068* (2013.01); *A61M 1/77* (2021.05);
(Continued)

(58) Field of Classification Search
CPC .......... A61M 5/30; A61M 37/00; A61M 5/32; A61M 39/105; A61M 1/0058; B67D 7/60; B65D 5/72; A61F 13/00068
See application file for complete search history.

(56) References Cited

U.S. PATENT DOCUMENTS 4,754,782 A  7/1988  Grantham
5,514,117 A  5/1996  Lynn
(Continued)

FOREIGN PATENT DOCUMENTS

DE  10107907 C1  5/2002
DE  102008008332 A1  8/2009
(Continued)

OTHER PUBLICATIONS

European Search Report dated Jan. 27, 2016 issued for priority European application 15002121.0. (9 pgs.) (The Search Report is in German.).

*Primary Examiner* — Benjamin J Klein
*Assistant Examiner* — Ilya Y Treyger
(74) *Attorney, Agent, or Firm* — Stinson LLP

(57) ABSTRACT

The invention relates to a device for connecting multi-lumen lines for the medical field, in particular for wound care in the field of vacuum therapy, having a preferably one-piece basic body, designed for tight and preferably releasable connection of at least two line lumens, wherein the basic body, for furnishing a distributor chamber for at least one, preferably two, three, or more lumens, opening into it, of the connected line and preferably at least one channel for removing a fluid from and introducing it into the distributor chamber, and when the line is connected, the distributor chamber is sealed off in fluid-tight fashion from at least one line lumen in such a way that a fluid exchange between the distributor chamber and this line lumen is prevented.

20 Claims, 9 Drawing Sheets

(51) Int. Cl.
*F16L 19/065* (2006.01)
*A61M 39/12* (2006.01)
*A61M 1/00* (2006.01)
*A61F 13/00* (2006.01)
A61M 37/00 (2006.01)
A61M 5/32 (2006.01)

(52) U.S. Cl.
CPC .............. *A61M 1/90* (2021.05); *A61M 39/12* (2013.01); *F16L 19/065* (2013.01)

(56) References Cited

U.S. PATENT DOCUMENTS

| | | |
|---|---|---|
| 7,678,102 B1 | 3/2010 | Heaton |
| 2008/0009832 A1 | 1/2008 | Barron et al. |
| 2008/0011368 A1 | 1/2008 | Singh et al. |
| 2010/0179493 A1 | 7/2010 | Heagle et al. |
| 2014/0236108 A1 | 8/2014 | Heaton |

FOREIGN PATENT DOCUMENTS

| | | |
|---|---|---|
| DE | 102008021312 A1 | 10/2009 |
| EP | 1398556 A2 | 3/2004 |
| EP | 2233814 A1 | 9/2010 |
| WO | WO 03/057070 A2 | 7/2003 | a. Cross section b. Side view

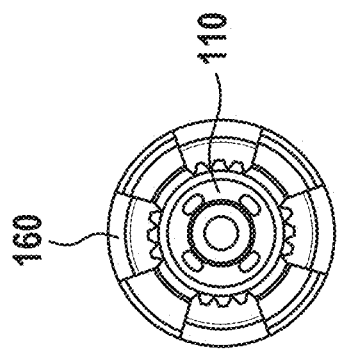
b. Cross section
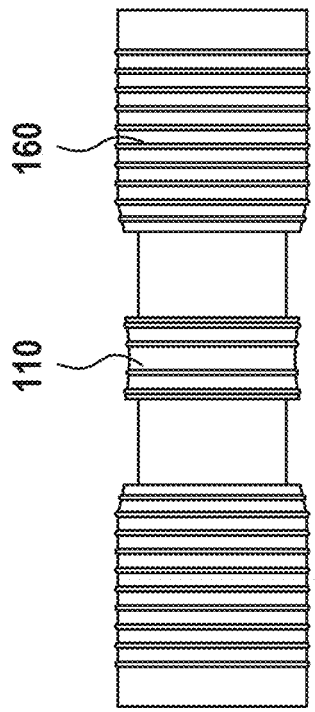
d. Connector with tension closure (the tube is firmly joined to the connector)
Fig. 5a
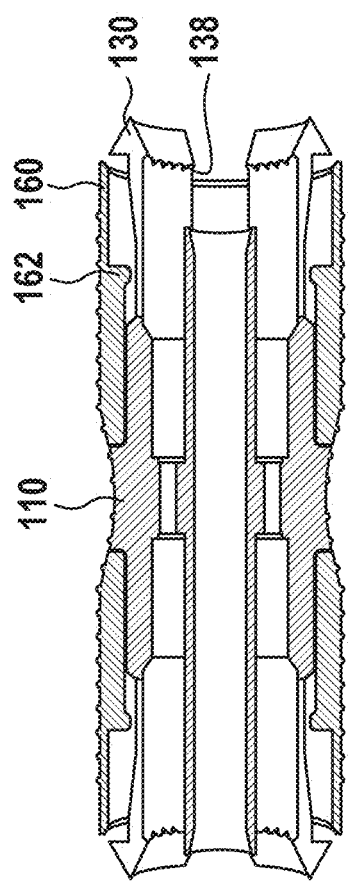
a. Full-section view of connector with tension closure (closed)
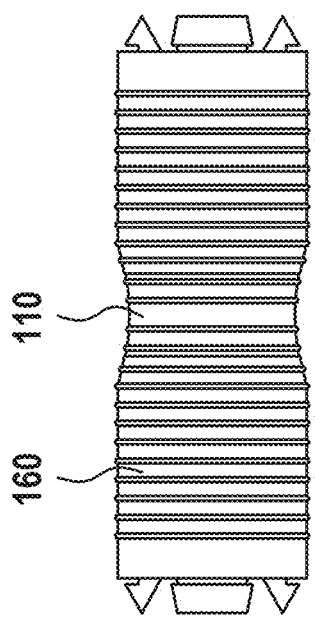
c. Connector with tension closure (the tube can be introduced)

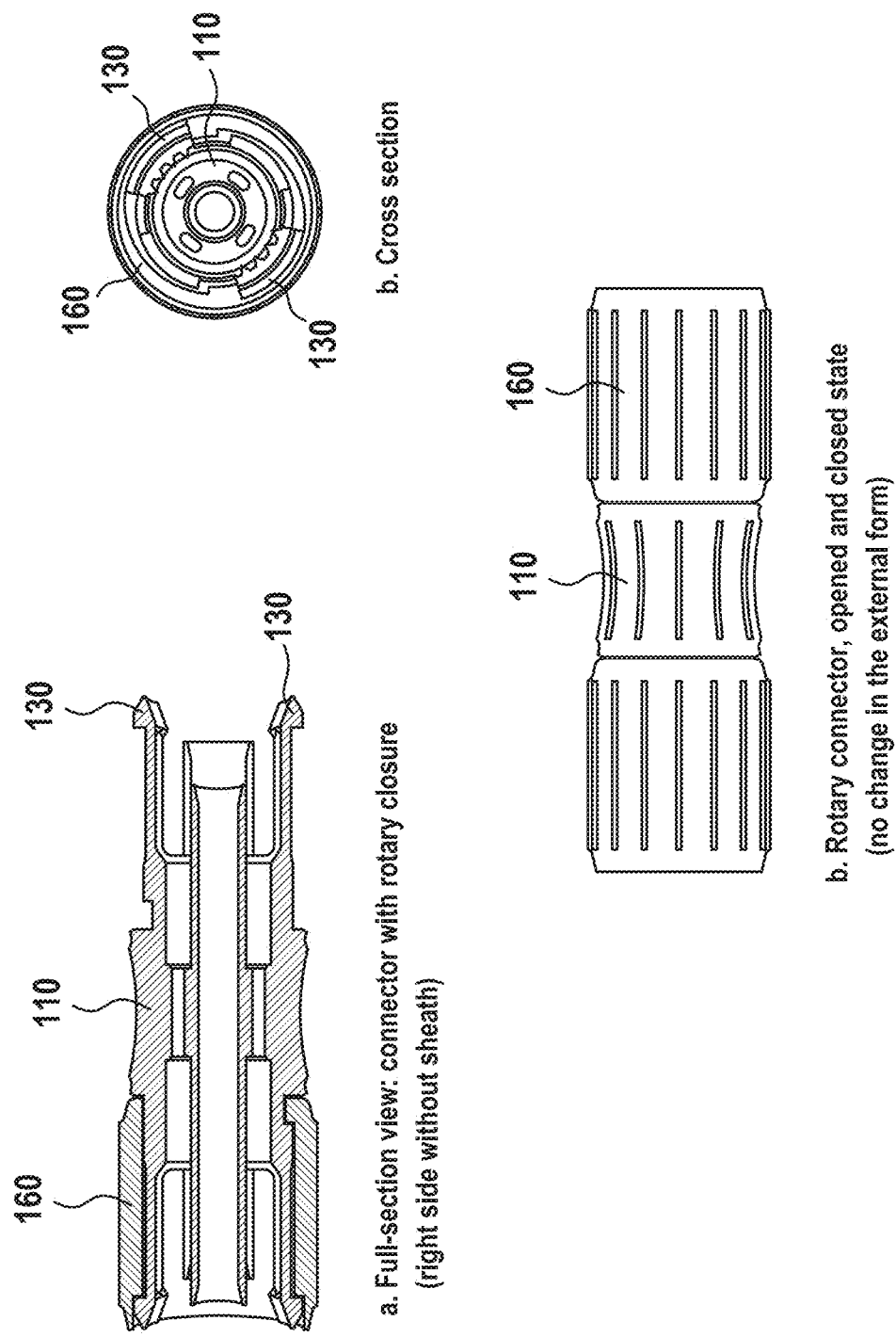

a. Full-section view: connector with pressure closure

Connector with pressure closure (the tube can be introduced)

WOUND CARE CONNECTION DEVICE AND WOUND CARE KIT

CROSS-REFERENCE TO RELATED APPLICATIONS

This application claims priority to and is a Continuation of U.S. patent application Ser. No. 15/211,172, filed on Jul. 15, 2016 which is based on and claims priority to European Patent Application Serial No. 15 002 121.0, filed on Jul. 16, 2015, each of which is incorporated herein by reference in its entirety.

STATEMENT REGARDING FEDERALLY SPONSORED RESEARCH OR DEVELOPMENT

Not applicable.

BACKGROUND OF THE INVENTION

The invention relates to a device for connecting multi-lumen lines in the medical field, in particular for wound care in vacuum therapy, having a preferably one-piece basic body designed for tightly and preferably releasably connecting at least two line lumens, and to a treatment kit for vacuum therapy having at least one connection device of the invention and at least one multi-lumen line connectable thereto.

In vacuum therapy, in order to promote the wound healing process, a vacuum is created in the area of a wound that is to be treated. To that end, the wound area is connected by a tube to a corresponding pump, with which exudate from the wound area can simultaneously be aspirated away. Additionally, it may be necessary to measure the pressure in the wound area via a separate line lumen, to ventilate the wound area via separate line lumens, and to supply wound cleaning agents, medications, or the like, etc. For individual indications, it may be advantageous to maintain a continuous flow in the area of the wound area. For other indications, it may be appropriate to maintain a constant vacuum. Finally, in some indications, it is also appropriate to generate and reduce the vacuum in a predetermined chronological order; that is, to apply an intermittent vacuum in the area of the wound area.

It has proved advantageous if two, three or more line lumens are used for ventilation, while the vacuum can be generated via a line lumen with a larger line cross section.

For the purpose of the vacuum therapy, the line lumens must be connected to a suitable vacuum therapy apparatus. Care should be taken that the connection on the one hand hold firmly, but on the other that it can be opened as needed manually/in controlled fashion easily, quickly, and in an uncomplicated way.

With the vacuum therapy apparatus, on the one hand the vacuum is generated and on the other, optionally ventilation, or ventilation and/or pressure measurement of the wound area and/or other of the tasks described above are performed. Moreover, in many cases it is necessary for two-, three- or multi-lumen lines to be connected to one another, for instance if the position of the vacuum therapy apparatus changes in relation to the patient and the length of the line has to be adapted accordingly. Already existing lines can then continue to be used, if extension lines with suitable devices are connected tightly to them.

In EP 2 240 233 B1, a two-part connection or connection device for the multi-lumen lines is described in which the individual lumens of the line are realized in the form of individual tubes. In this device, the individual tubes of a multi-lumen line are brought into engagement in sealing fashion with a plurality of inner tube connection plug elements in a portion of an internal connection part; the individual inner tube connection plug elements are brought into engagement with outer tube connection tap elements, to which the individual tubes of the other multi-lumen line are connected. In these connection devices, two connection pieces must be joined together and also joined to the individual tubes of the multi-lumen lines by the user.

A connection device for a multi-lumen tube, in which the lumens are located in the interior of the line or tube, is described in EP 2 240 234 B1. This known device is in two parts and contains a connection piece to be inserted and a receiving connection piece, each piece having a plurality of flow channels, which must correspond exactly to the number and the shape and dimensions design (round, oval; diameter, etc.) of the lumens present in the line. In EP 2 536 448 B1, a coupling part for separate tubes is described, which has a device that enables fluid delivery from a service channel into a drainage channel but prevents fluid from flowing in the reverse direction.

In WO 2010/127461 A1, a two-piece coupling arrangement is described, with which multi-lumen tubes (preferably those that have a central drainage line and three additional lines arranged around that drainage line) can be connected to one another. Both the drainage line and the additional lines can discharge into a common chamber in order to measure the pressure there. In a connection device of U.S. Pat. No. 8,002,313 B2, a chamber is provided in which the lumens of a first and second tube can communicate with one another, even when the tubes are mounted radially offset from one another.

It is also prior art to realize multi-lumen lines in the form of tubes that are penetrated axially by a plurality of lumens. In that case, it is no longer necessary to join individual tubes to one another. Instead, it suffices to connect just one multi-lumen tube. In these known multi-lumen tubes, a central lumen may be provided, which extends coaxially to the tube axis. Further lumens of the tube can be located radially offset from one another and penetrate the tube sheath, defining the central lumen, in the axial direction parallel to the tube axis. It is especially advantageous to have an odd number of additional lumens, especially preferably three additional lumens. The radially offset additional lumens can be equipped with a smaller cross section than the central lumen. Two, three or more radially located, circumferentially offset additional lumens may be provided. When such multi-lumen tubes are connected, in particular when such multi-lumen tubes are joined, care must be taken that the individual lumens of the one tube communicate fluidically with the corresponding lumen of the other tube, without there being an unwanted connection between tube lumens that serve different purposes. For instance, in many cases care must be taken that the central lumen used to generate the vacuum not enter into communication with the radially offset additional lumens, and at the same time, the radially offset additional lumens of the multi-lumen tubes to be joined together must be joined to one another as well.

This joining proves problematic in many cases, because it requires a positionally correct location of the individual tube lumens relative to one another, especially the radially offset additional lumens, which extend eccentrically, or in other words non-concentrically, to the tube axis. The individual radially offset additional lumens can be located on a circumference of the tube sheath, the circumference being concentric with the tube axis.

BRIEF SUMMARY OF THE INVENTION

In view of these problems in the prior art, the object of the invention is to furnish a connection device for multi-lumen lines for wound care, in particular in the field of vacuum therapy, which enables simple connection of the lines while reliably ensuring the desired separation among individual line lumens.

According to the invention, this object is attained by a refinement of the known connection devices, which is characterized essentially in that the basic body is designed to furnish a distributor chamber for at least one lumen of the connected line, the at least one lumen opening into that chamber, and preferably to furnish at least one channel for removing and introducing a fluid from or into the distributor chamber, and when the line is connected, the distributor chamber is sealed off in fluid-tight fashion from at least one line lumen in such a way that a fluid exchange between the distributor chamber and this line lumen is prevented.

The invention is based on the recognition that the connection or communication of multi-lumen lines need not take place via direct connection of the individual line lumens or by direct communication of the individual line lumens; it can also happen with an interposed distributor chamber. By incorporating such a distributor chamber, a reliable communication can be effected even without exact alignment of the individual lumen orifices. For instance, it is possible for individual eccentrically located additional lumens of a multi-lumen tube to discharge into a common distributor chamber, which is sealed off from a communication region for a central lumen of the tube. On the other hand, the channel provided for introducing a fluid into or removing it from the distributor chamber can discharge into a different distributor chamber, which in turn is in communication with orifices of eccentrically located additional lumens of a different multi-lumen tube. In this way, the radially offset additional lumens can be made to communicate fluidically by the interposition of at least one distributor chamber, without requiring the individual radially offset additional lumens to be aligned with one another in a predetermined rotary position.

In the context of the invention it is also possible to join tubes to a variable number of radially offset additional lumens. If one end of a tube, having three radially offset additional lumens, opens into the distributor chamber and on the other side one end of the tube is to be joined together with a different number of radially offset additional lumens, such as five additional lumens, a reliable fluid exchange can take place between the additional lumens via the distributor chamber.

Moreover, it is possible for such tubes to communicate with one another while avoiding an unwanted fluid exchange, where two, three or more "central" lumens are surrounded by radially offset additional lumens; the central lumens are also separate from one another and from the radially offset additional lumens.

The term "fluid" in the context of the present invention disclosure means a liquid and/or a gas.

In addition to the distributor chamber, optionally formed together with the line, the basic body can have at least one connection fitting, designed for connecting at least one line lumen, in particular the central lumen of a multi-lumen tube, which connection fitting is preferably designed for introduction into at least one line lumen, in particular the central line lumen of the multi-lumen tube. The distributor chamber can surround the connection fitting at least partially, preferably completely. With the aid of the connection fitting, a reliable separation between the central lumen and the radially offset lumens of a multi-lumen tube is ensured. For connecting tubes with two, three or more central lumens, an equivalent number of connection fittings may be provided.

If the basic body has a channel for introducing and removing a fluid into and from the distributor chamber, then the channel can be formed in a collar that at least partly surrounds the connection fitting. The collar widens the connection fitting radially. The channel located therein can extend approximately parallel to the connection fitting and the tube axis or line axis of the connected line.

It has proved especially advantageous if the distributor chamber is defined by a chamber bushing beginning at the collar and extending approximately parallel to the connection fitting, and if between the connection fitting and the chamber bushing, an annular gap is designed for receiving a sheath, penetrated by at least one lumen, of a multi-lumen line. The axial end, facing away from the collar, of the connection fitting and/or of the chamber bushing can be chamfered to facilitate introducing a multi-lumen tube; the inside diameter of the chamber bushing optionally tapers beginning at its end facing away from the collar, in the direction of the collar, or the outside diameter of the connection fitting, beginning at the end facing away from the collar, increases in the direction of the collar, so that the width of the annular gap decreases in the direction of the collar.

When devices of the invention are used for connecting multi-lumen lines, the distributor chamber can be embodied especially simply if a stop is provided that limits the introduction of the sheath into the annular gap, is located at an axial spacing from the collar, and is preferably embodied as a radial shoulder on the connection fitting and/or of the chamber bushing. Then the distributor chamber is defined by the fitting, the chamber bushing, the collar, and the sheath end face contacting the stop; an axial spacing between the collar and the sheath end face is specified by the position of the stop.

In particular in this last-described embodiment of the invention, it has proved expedient if the basic body is made at least partly of transparent material and/or has a window, so that the introduction of the tube end into the annular gap can be observed and monitored. It has proved especially appropriate if the basic body, at least in the vicinity of the stop, is formed of transparent material and/or is equipped with at least one observation window. As already mentioned above, the connection fitting serves as a seal between the central lumen of a multi-lumen tube and the radially offset additional lumens, which discharge into the distributor chamber. Furthermore, with the aid of the connection fitting, a sealing separation between the distributor chamber and the central tube lumen is also effected. The sealing closure can be effected especially simply and reliably if the connection fitting tapers in the direction toward its axial end facing away from the collar, so that when the central lumen is slipped onto the connection fitting or when the connection fitting is introduced into the central lumen, the central lumen is stretched. As a result, a firm seat of the central lumen on the connection fitting is achieved, and the sealing effect develops.

Sealing the distributor chamber from the environment can be achieved if a sealing device is provided which when the sheath is introduced into the annular gap comes into contact with an end face of the sheath; the sealing device expediently comes into contact only with a radially outer ring of the end face, without closing the radially offset additional lumens of the tube connection, as will be explained hereinafter in conjunction with FIG. 4c. In addition or alternatively, for sealing off the distributor chamber from the environment, the connection device of the invention can have a sealing device that preferably completely surrounds the sheath and that, when the sheath is introduced into the annular gap, comes into contact with an outer boundary face, surrounding the line axis, of the sheath. This sealing device can have a sealing shell that is received in the annular gap between the connection fitting and the chamber bushing and has at least one and preferably two, three or more axially spaced-apart sealing lips or lamellas that surround the bushing axis and come into contact with the outer boundary face of the sheath. These sealing lips or lamellas can be embodied elastically and can be injected by an injection-molding process into a solid sealing shell body. Then, the fixed sealing shell body on the one hand and sealing lips or lamellas on the other enter into a solid connection with one another. The thus-formed sealing shell can then be introduced into the basic body.

The sealing shell can be clipped into a surrounding inner groove of the chamber bushing via an annular snap connection, to obtain a positive connection. In addition or alternatively, it may also be joined to the basic body materially or nonpositively. However, the above-addressed positive connection between the sealing shell and the chamber bushing has proved especially expedient. If the sealing shell has two, three or more axially offset sealing lips, then a pressure gradient occurs between the individual chambers defined by the sealing lips, which ensures an especially tight communication or connection of the multi-lumen line.

With regard to the annular snap connection, the sealing shell on its radially outer sheath face preferably has an annular bead that is complementary to the inner groove of the chamber bushing and surrounds it azimuthally. The embodiment may be made such that this annular bead enters into a fluid-tight engagement with the inner groove. Alternatively, however, it may be advantageous to provide an axial interruption or opening in the annular bead, at at least one point and preferably at two diametrically opposed points. As a result, it is true that the tightness of the engagement between the bead of the sealing shell and the groove of the chamber bushing is undone. However, it is then possible for an ethylene dioxide (EO) sterilization to take place through the interruption or opening.

For relieving the sealing communication between the connection device on the one hand and the multi-lumen line on the other, it has proved especially advantageous if a securing device that is adjustable between a release position, which enables the connection of the multi-lumen line, and a preferably acoustically confirmable securing position, which secures the connected line to the basic body, is provided. This securing device can be embodied on the order of a clamping mechanism, with which the line lumen is held on the connection device independently of the sealing connection. This securing device can have a clamping bushing which extends coaxially to the chamber bushing and is rotatable and/or axially displaceable between the release position and the securing position. The clamping bushing can cooperate with a clamping body which is mounted on the basic body of the connection device and which, in the securing position, is forced against the outer boundary face of the line.

The clamping body can have at least one clamping tongue, embodied preferably in one piece with the chamber bushing and from there extending approximately parallel to the bushing axis in the direction of an axial end of the connection device, and the end of the clamping tongue remote from the chamber bushing is forced radially inward toward the bushing axis into the securing position by adjusting the securing device.

The clamping action can be brought about especially simply and reliably if the clamping bushing has a clamping ramp associated with the respective clamping tongue that, from where the ramp begins, rises in the direction of the end of the ramp in direction of the bushing axis and comes into contact with a radially widened region of the clamping tongue, so that an adjustment of the clamping bushing causes a displacement of the ramp relative to the clamping tongue, as a result of which a raised area of the clamping tongue is offset radially inward, beginning when it is in contact with the beginning of the ramp, in the direction of where it is in contact with the end of the ramp. The ramp in the clamping bushing can extend circumferentially. In this embodiment of the invention, the clamping action is brought about by a rotary motion of the clamping bushing by means of the bushing axis. Alternatively or in addition, the clamping ramp can extend in the axial direction. Then, the clamping action is effected by an axial motion of the clamping bushing (push or pull motion).

In all the embodiments of the invention, it has proved expedient if the motion of the clamping bushing is limited by a stop. When the clamping bushing comes into contact with the stop, a noise can be produced, in order to provide an acoustical confirmation of closure. For especially secure clamping, it has proved especially expedient if the clamping action wanes somewhat when the securing position is reached, so that the clamping bushing can be moved in reverse into the release position again only counter to a (slight) force exerted from outside. This can be attained for instance by providing that the ramp end, on reaching the securing position, slides over the apex of the radially raised area of the clamping tongue, so that the clamping tongue has reached its maximum deflection inward even before reaching the securing position, and springs back again somewhat in the securing position.

To facilitate adjusting the securing device from the release position into the securing position, the clamping tongue can be placed, with an intentional bending point, against the chamber bushing. The intentional bending point can be embodied as a thinning of material at the transition between the chamber bushing and the clamping tongue.

As already explained at the outset, generic connection devices are also used to furnish an optionally separable connection for multi-lumen tubes. Known connection devices, which enable that kind of connection, have at least two parts, which have to be joined tightly together by the user in order to be able to establish a communication of the tubes with one another. In these known devices, the various parts are typically firmly joined to the respective tube ends (for instance by gluing). During vacuum therapy, however, it is often necessary for the tubes that connect the vacuum therapy apparatus and the wounds to be shortened at an arbitrary point and rejoin them, for example whenever the position of the apparatus changes in relation to the patient. Moreover, an easy exchange, for instance of the part of a tube toward the wound or toward the pump, should be ensured. In connection devices that comprise two or more parts to be joined together, however, this is possible only with difficulty. This is especially true if the individual parts of the devices are solidly joined to the ends of the tubes.

If the connection device of the invention is designed for joining multi-lumen lines with two, three or more lumens, it has proved expedient if the basic body has two, three or more connection fittings, each of which can be introduced into a central lumen of a line and are joined together and/or is designed for furnishing two, three or more distributor chambers, of which preferably at least two can be joined together via at least one channel.

In this way, a one-piece connection device is furnished that makes it possible to shorten tubes at an arbitrary point and rejoin them, which makes for easier use, enables more-flexible treatment, and reduces costs. Moreover, the safety of the system is enhanced, since because the device is in one piece, the user no longer has to seal the area joining the separable parts of the known connection device. This minimizes the risk of user error. Within the scope of this invention, the term "one-piece connection device" is used for a device such that the user is able to join all the necessary tube ends together without having to join individual device parts together beforehand. In the process the tubes are joined by joining the tube to a connection region of the connecting device, for instance by slipping a central tube lumen over onto a connection fitting of the device.

In a one-piece connection device of this kind according to the invention for connecting multi-lumen tubes, connection fittings extending from the collar in opposite directions from one another can be provided which are each surrounded by a chamber bushing, beginning at the collar and extending in opposite directions, creating two annular gaps between the connection fittings on the one hand and the chamber bushings on the other; their orifices face away from one another, and a seal can be inserted into each of them. Each of the chamber bushings can be assigned a clamping bushing, and the clamping bushing can be displaced independently of one another between a securing position and a release position. Between the clamping bushings, outer boundary faces of the basic body of a connection device of the invention that are out in the open can be provided, which makes using the clamping bushings easier. The exposed area of the basic body can surround the collar and can have a concave contour, in order to facilitate access to it. If a connection device for three multi-lumen tubes according to the invention is to be used, the connection fittings can extend, beginning at a central region, in the shape of a Y in different directions. The correct clamping bushings can then be assigned to each connection fitting. The axial length of the connection fittings is the same or different, depending on the desired behavior of the various embodiments in use.

To avoid injuring a patient in the event of an unintended movement of the vacuum therapy apparatus, it has proved expedient if the forces required to release the lines from the basic body, when a securing device has been displaced in the securing position, differ from one another for at least two securing devices. This can be attained for instance by providing that the connection fitting is embodied in various lengths. If the connection fitting extends as far as the clamping point of the securing device, which is optionally determined by clamping hooks of the clamping tongues, the securing device withstands stronger tensile forces on the tube than in a shorter embodiment of the connection fitting. Expediently, the clamping at the end of the connection device of the invention toward the vacuum therapy apparatus is lessened. Other possibilities for attaining the same effect would be for instance be different thicknesses/degrees of tapering of the connection fittings, seals of varying softness, different clamps, different shape of the clamping tongues, the clamping height, etc. Alternatively or in addition, different release forces can be attained by means of different thicknesses/degrees of tapering of the connection fittings, seals with different moduli of elasticity, different clamping rings, and/or different clamping mechanisms.

As can be learned from the foregoing explanation of connection devices of the invention, a treatment kit of the invention has at least one connection device and at least one multi-lumen tube connectable to it; the tube can have a central lumen, defined by a tube sheath, and at least one additional lumen which penetrates the tube sheath in a direction extending parallel to the tube axis and parallel to the central lumen; the at least one additional lumen, after connection to the connection device, opens into the distributor chamber, and/or the connection fitting can be introduced into the central lumen. The tube preferably has a central lumen as well as three symmetrically arranged additional lumens.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

The invention will be explained below in conjunction with the drawings, to which reference is made regarding all details essential to the invention that are not described in detail in the specification. In the drawings:

FIG. 1a is a radial sectional view of a multi-lumen tube for a treatment kit according to the invention for vacuum therapy and FIG. 1b is an axial sectional view of the tube of FIG. 1a;

FIGS. 5a-5c show securing devices for connection devices of the invention;

DETAILED DESCRIPTION OF PREFERRED EMBODIMENT

Figure 1A:
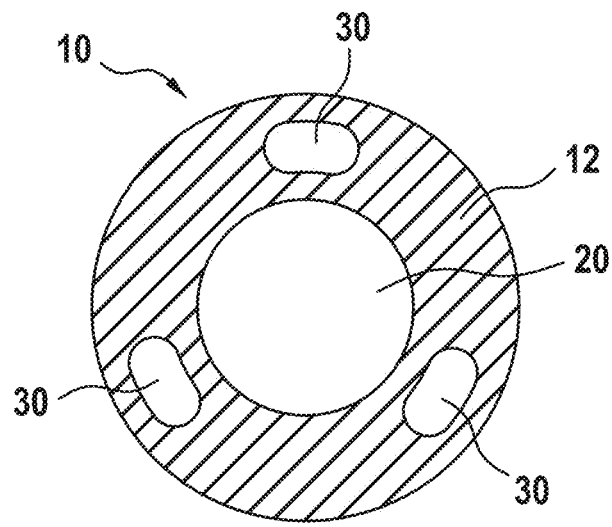
Figure 1B:
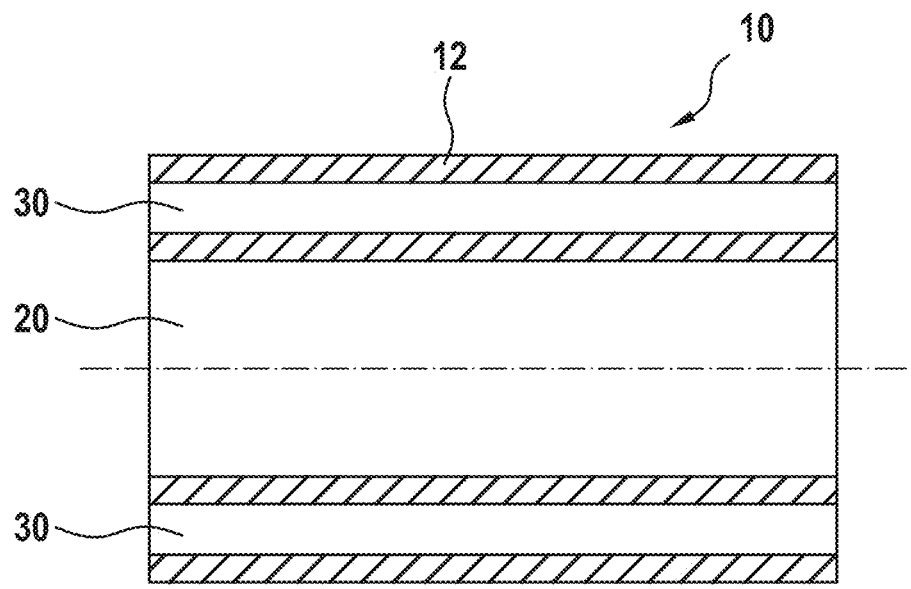

FIG. 1a shows a radial sectional view of a multi-lumen tube that can be used for a kit according to the invention. FIG. 1b shows an axial sectional view of the tube of FIG. 1a. The multi-lumen tube, indicated as a whole by reference numeral 10 and having a multi-lumen line, has a central lumen 20 surrounded by a tube sheath 12. The tube sheath 12 is penetrated by a number of additional lumens 30 located radially offset from the central lumen 20. The additional lumens are offset uniformly from one another in the circumferential direction. They have a smaller cross-sectional area than the central lumen 20. The centers of the radially offset additional lumens 30 are located on a circumference that extends coaxially to the tube axis.

In kits of the invention, the central lumen 20 can be used to create a vacuum in the wound area and to aspirate exudate away from the wound area, while the radially offset additional lumens 30 can be used for instance to ventilate the wound area for pressure measurement, and/or for delivering medication and cleaning fluids, etc. The central lumen 20 on the one hand and the radially offset lumens 30 on the other must be separated from one another, at least along the way between the vacuum therapy apparatus and the wound area.

In preferred multi-lumen tubes of the invention, a central lumen 20 and an odd number of symmetrically arranged additional lumens 30, radially offset from the central lumen 20, are provided. This ensures an especially secure connection of the wound to the vacuum therapy apparatus, since as a result of this geometry, even if the tube becomes clamped or kinked, at least one of the additional lumens will merely be minimally deformed; thus in a pressure measurement, for instance, there will be no loss of information and also, there is no need to fear a disruption of communication (for instance when ventilating the wound).

The tube geometry shown in FIG. 1, with three symmetrically arranged, radially offset additional lumens, has proved especially advantageous. With this geometry, if kinking occurs, only one or two of three lumens will be significantly deformed, and the shear forces inside the tube in the event of clamping and kinking have a minimal effect on the passability of the lumens.

Figure 2:
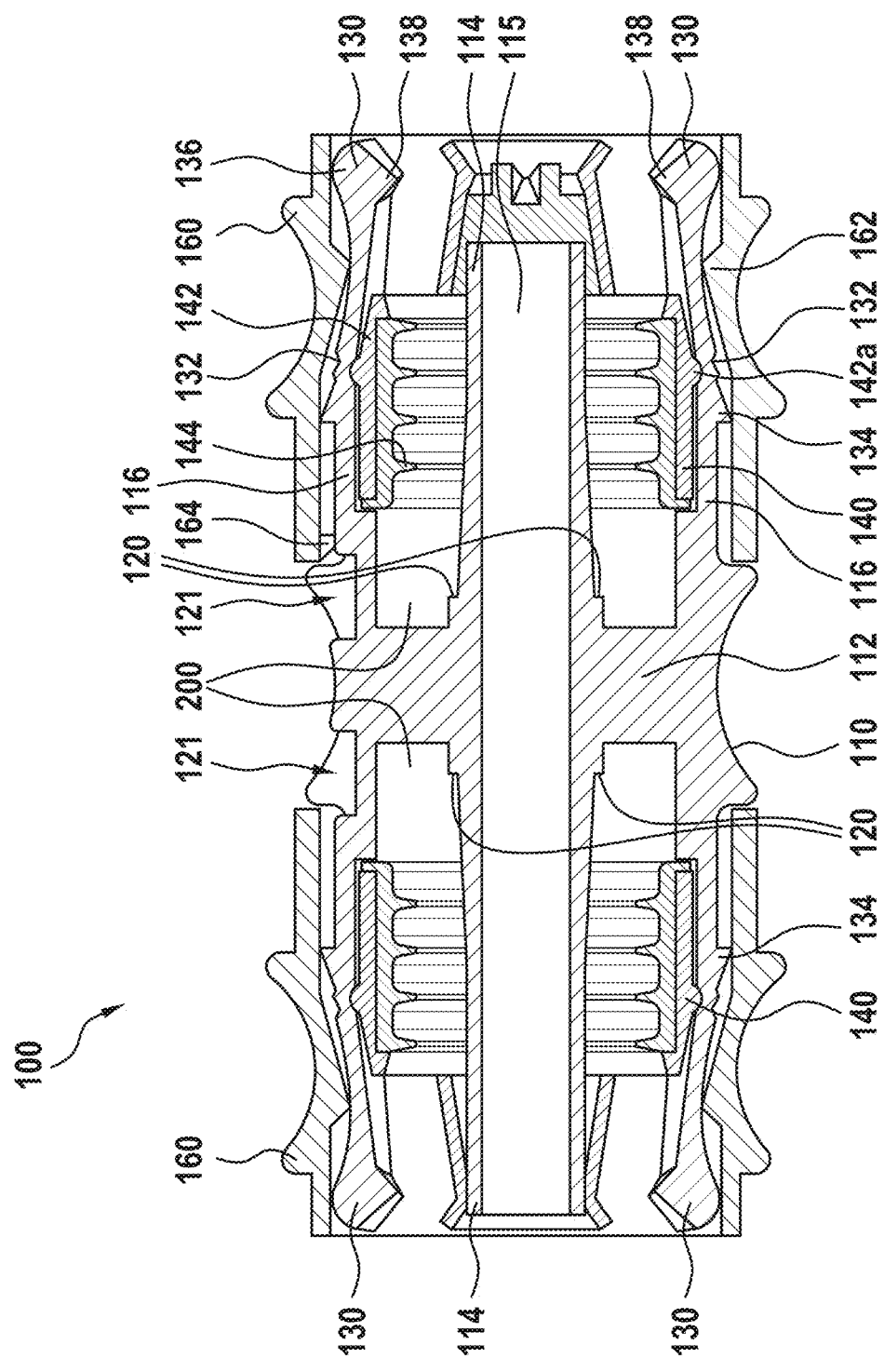
FIG. 2 is a view of a first embodiment of a connection device of the invention.

The connection device shown in FIG. 2 is designed for connecting two multi-lumen tubes of the type shown in FIG. 1. The connection device, identified overall by reference numeral 100, includes a basic body 110, two sealing shells 140, and two clamping bushings 160.

The basic body 110 has a central collar 112, beginning at which two connection fittings 114 extend coaxially to one another in opposite directions from one another. The connection fittings 114 are penetrated by a continuous bore 115. The collar 112 surrounds the connection fittings 114 completely. At a radial spacing from the connection fittings 114, chamber bushings 116 are placed against the collar 112. The chamber bushings 116 extend coaxially to one another and coaxially to the connection fittings 114 in directions opposite one another, beginning at the collar 112. Between the chamber bushings 116 and the connection fittings 114, annular gaps are formed, into which the sheath 12 of the multi-lumen tube 10 can be introduced. The insertion depth of the tube into the annular gap is limited by stops 120, which on their ends facing toward the collar 112 are embodied as radially widened areas of the connection fittings 114. As indicated at 121, the chamber bushings, in the vicinity of the collar or of the stops 112, are equipped with windows, which enable visual monitoring of the contact of the end faces of the tube 10 with the stops 120.

The sealing shells 140 are inserted into the annular gaps formed between the connection fittings 114 and the chamber bushings 116, so that the outer boundary faces of the sealing shells, with the aid of a ring snap connection, rest in positive fashion on the inner boundary face of the chamber bushings. The sealing shells 140 include a rigid or nondeformable sheath body 142, for instance of polypropylene, and a plurality of axially spaced-apart deformable sealing lamellas 144, which when the line 10 has been thrust in rest on the outer boundary face of the line and thus form a multi-chamber seal. In other embodiments of the invention, it is possible for only a sealing lamella to be provided. On the outer boundary face of the rigid sealing shell 142, an encompassing bead 142a is formed, which to form the ring snap connection is received in a radially inner indention of the chamber bushing 116.

Figure 7:
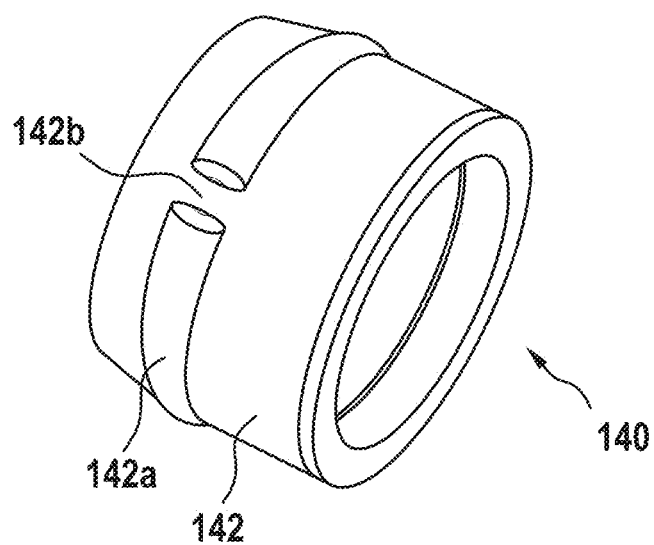
FIG. 7 shows one embodiment of a sealing shell.

FIG. 7 illustrates an embodiment in which the bead 142a is not embodied as completely surrounding but instead has two diametrically opposed interruptions or openings 142b. This allows the passage of sterilization gas in ethylene dioxide (EO) sterilization.

Within the scope of the invention, the use of a rigid sheath body is not absolutely necessary. The seal can also be made in some other way. For instance, it can be glued, injected directly, or implemented in the form of a commercially available seal. Moreover, it is not absolutely necessary that the sealing lamellas be deformable. It suffices if the tube is resilient. Then the tube forms the sealing body, which conforms to a rigid structure of the sealing shell. The insertion depth of the sealing shells 140 is limited by a stop of the chamber bushings. In this area, the sealing body that has the sealing lamellas fits over the end face of the rigid sealing shell 142, to enable face-end sealing of the annular gap between the connection fittings 114 and the chamber bushings 116.

Figure 3:
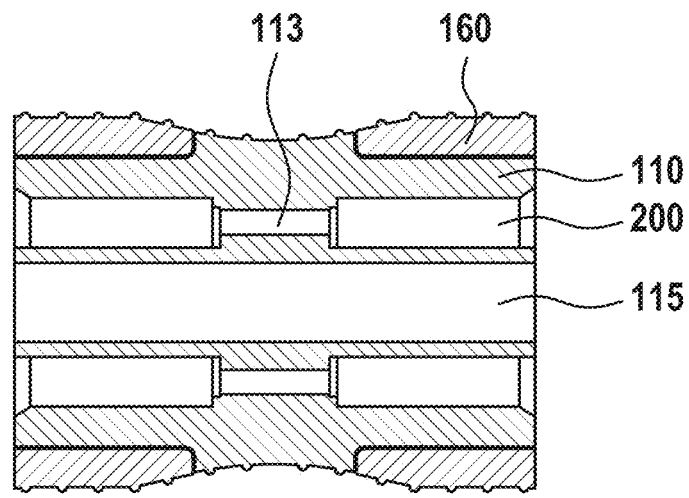
FIG. 3 is a schematic detail view of a connection device of the invention.
Figure 4A:
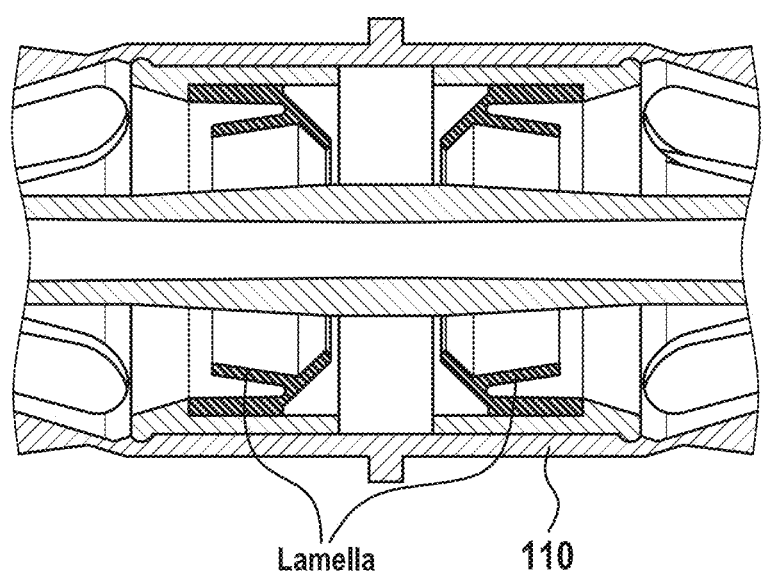
FIGS. 4a-4e show sealing devices for a connection device of the invention.
Figure 4B:
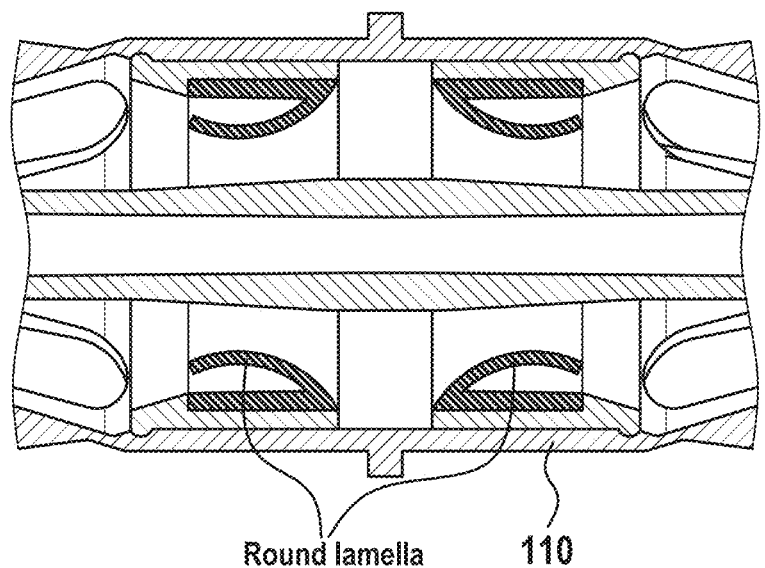
Figure 4C:
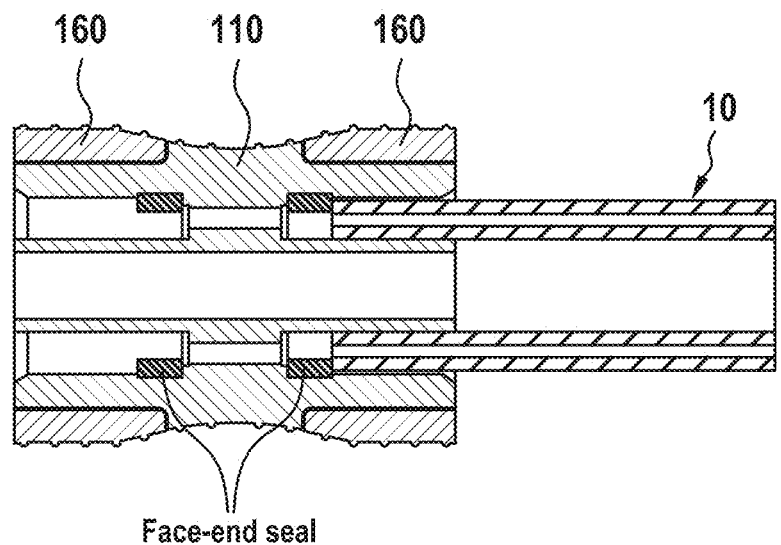
Figure 4D:
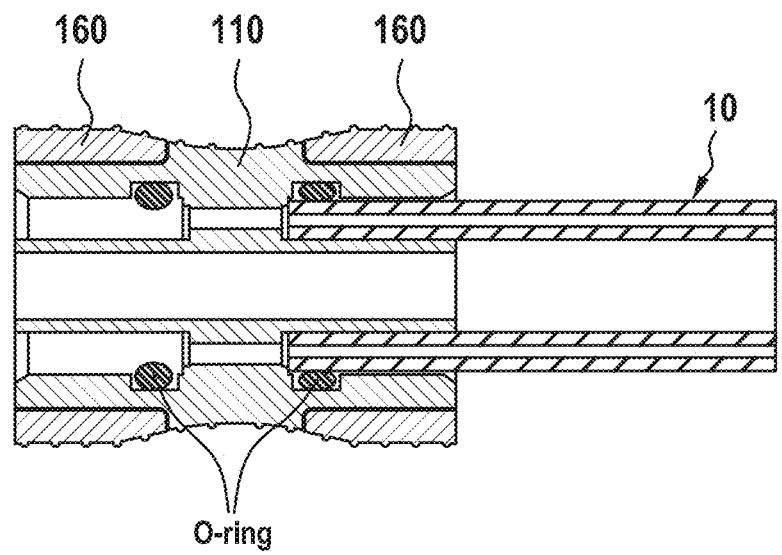
Figure 4E:
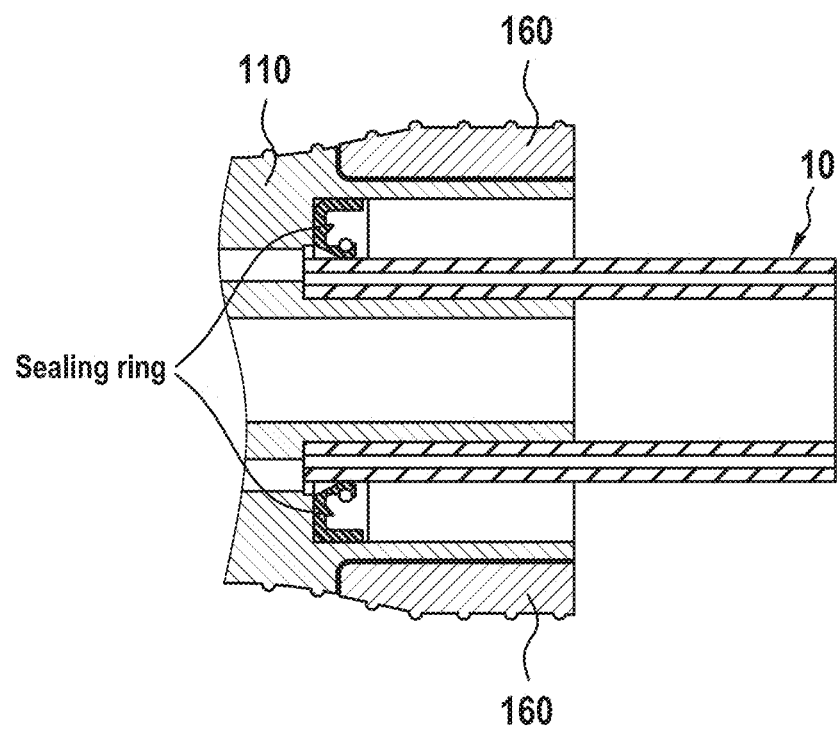

Between the stops that limit the insertion depth of the tube into the annular gap and the surrounding collar 112, a distributor chamber 200 is formed once the tube has been inserted. The distributor chambers 200 formed on both sides of the collar 112 communicate with one another via channels 113 (see FIG. 3). It is thus possible to join the radially offset additional lumens 30 of the tube sheaths 12, inserted into the annular gaps, to one another regardless of the rotary position of the sheaths relative to the connecting device; sealing the radially offset additional lumens from the central lumen 20 is made possible with the aid of the connection fittings 114. The connection fittings 114 are introduced into the central lumen 20 of the tubes when the tubes 10 are connected. The outer boundary faces of the connection fittings 114 broaden, beginning at the ends facing away from the collar 112 and extending toward the collar, so that the central lumen 20 is widened upon introduction of the connection fittings 114, and a tight seat of the tubes 10 on the connection fittings 114 is achieved; at the same time, sealing occurs from contact of the sealing lamellas 144 with the outer boundary face of the sheath 12.

On the chamber bushings 116, on their ends facing away from the collar 112, clamping tongues 130 are located, which are placed against the chamber bushings 116 via areas of thinned material 132. The chamber bushings 116 and clamping tongues 130 are surrounded by clamping bushings 160. In the embodiment of the invention shown in FIG. 2, the clamping tongues 130, on their ends facing away from the chamber bushings 116, have thickened areas 136 that radially widen the clamping tongue 130. In addition, radially on the inside, the clamping tongues 130 are provided with clamping teeth 138 that become wider radially inward. The clamping bushings 160 are equipped on the inner boundary faces with radially inner clamping rings 162 that reduce the inside diameter of the clamping bushings 160. When the clamping bushings 160, beginning at the release position shown in FIG. 2, which enables the introduction of the multi-lumen tube into the annular gaps between the connection fitting 114 and the chamber bushing 116, are pushed away from the collar 112, the clamping rings 162 come into contact with the thickened area 136 and press the clamping tongue 130 as a whole radially inward; shifting the position of the clamping tongues 130 is facilitated by the intentional bending points 132 in the transition region between clamping tongues 130 and chamber bushings 160.

In the course of the axial motion of the clamping bushing 160 relative to the clamping tongue 130, the clamping ring 162 slides over the apex of the thickening 136, so that a return motion from the securing position thus reached to the release position shown in FIG. 2 is possible only by overcoming a thrusting force. Upon reaching the securing position, radially inner stop ribs 164 of the clamping bushing 160 come into contact with radially outer stop ribs 134 of the chamber bushing 116, so that reaching the securing position is confirmed acoustically. In the securing position, the clamping teeth 138 engage the outer boundary face of the tube sheath 12, so that the tube sheath is secured against coming loose from the connection device 100. As can be seen in FIG. 2, in the release position as well, the clamping bushings are located at an axial spacing from one another that is defined by the collar 112 with radial widening. This makes separately actuating the clamping bushings 160 easier. The collar 112, on its outer boundary face, has an indentation that eases access to the basic body.

As can also be seen in FIG. 2, the connection fittings 114 of the basic body 110 are embodied in various lengths. It is thus attained that the forces required to release the tubes from the connection fittings are unequal. The clamping bushings can be embodied as rounded on the face end, in order to prevent their catching on other objects. Conversely, in alternative embodiments, the lengths of the connection fittings 114 are equal. Markings that indicate the possible directions of motion can be made on the outer boundary faces of the clamping bushings. These markings can be embodied for instance in the form of axial double arrows, labels (up/down) and/or symbols (padlock, etc.). The markings can be embodied as raised/indented and optionally roughened/polished surface regions or simply painted on, glued on, etc., in order to facilitate the use of the connection device. The surface regions of the clamping bushings can be roughened and/or can contain grooves, rings, structured areas, etc. (or even have no marking), to prevent a person's finger from slipping in use.

In FIG. 4, variations of possible seals between the multi-lumen tube and the basic body of a connection device of the invention are shown. FIG. 4a shows a polygonal lamella seal; FIG. 4b shows a seal with a round lamella; FIG. 4c shows a face-end seal outside the radially offset additional lumens between the end faces of the tubes and collar 112. FIG. 4d shows a seal via sealing rings embodied as O-rings. Finally, as in FIG. 4e, a radial shaft seal can also be used.

Figure 5C:
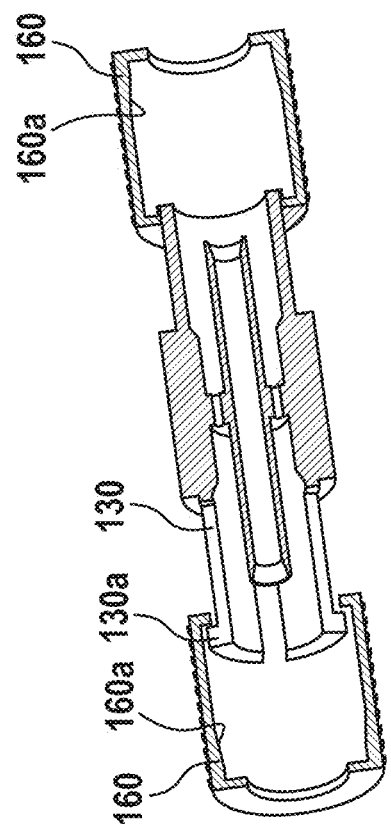
Figure 5C:
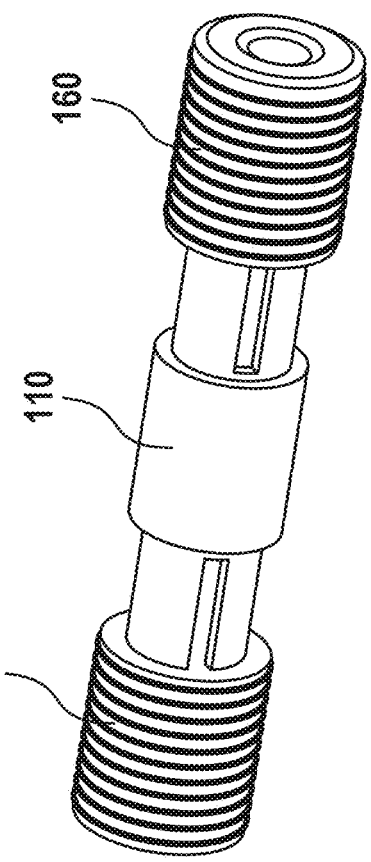

In FIG. 5, variations of securing devices of connection devices of the invention are shown. FIG. 5a essentially corresponds to the securing device of FIG. 2; a radially inner clamping ring 162, upon displacement of the clamping bushing 160 from the release position to the securing position, slides along radially widening clamping ramps of the clamping tongues 130 and offsets the clamping tongues 130 radially inward; the clamping teeth 138 enter into engagement with the outer boundary face of the tube sheath 12. In the embodiment shown in FIG. 5a, in all four clamping tongues 130 spaced apart from one another in the circumferential direction are provided; with the aid of the axial motion of the clamping bushing 160, they can be forced against the outer boundary face of the tube sheath 12. The clamping bushings 160 are pulled apart in the process, which can be seen by comparing the various views in FIG. 5a. The securing position of the securing device is shown at bottom right.

In the embodiment of the invention shown in FIG. 5b, the securing position is reached by rotation of the clamping bushing. To that end, in the vicinity of the inner boundary face of the clamping bushing, clamping ramps extending in the circumferential direction are provided, which by rotation of the clamping bushing bring about radial shifting of the clamping tongues 130. An advantage of this embodiment of the invention is the reduced space required.

Finally, the clamping tongues in the embodiment of FIG. 5c can be radially offset inward by axially compressing the clamping bushings 160. To that end, corresponding clamping ramps 160a are provided on the inner boundary face of the clamping bushings 160 and cooperate with thickenings 130a on the outer boundary faces of the clamping tongues 130.

Figure 6:
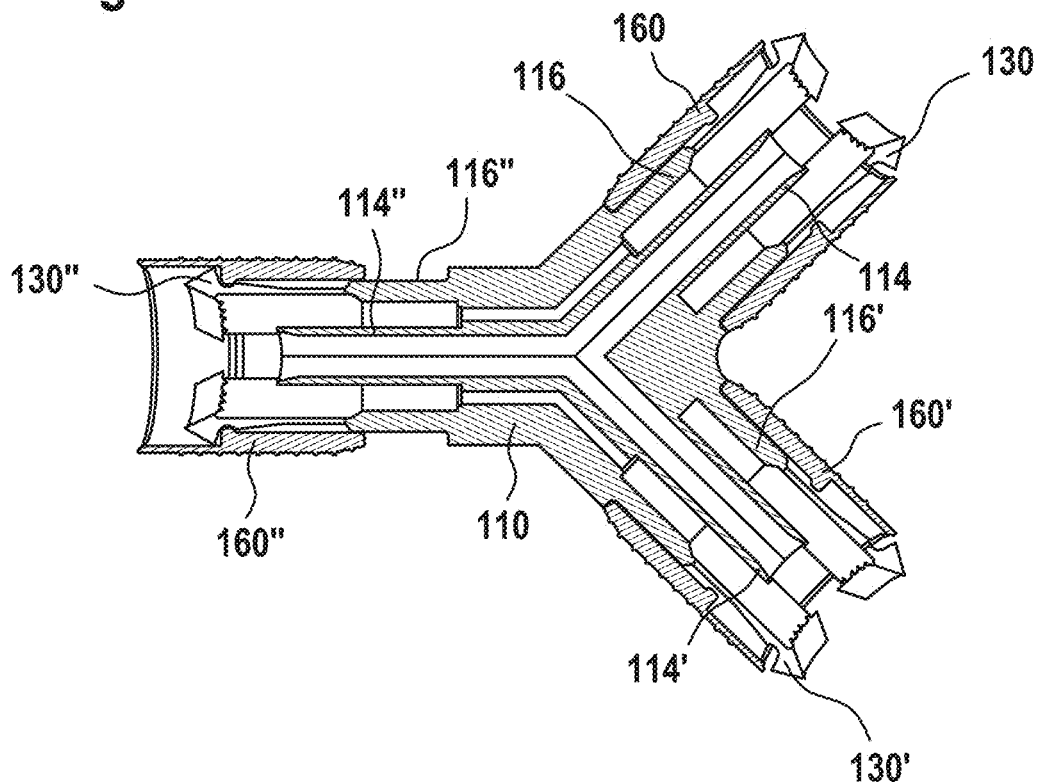
FIG. 6 shows a further embodiment of a connection device of the invention.

The connection device of FIG. 6 is intended for a total of three multi-lumen tubes. For that purpose, the connection device of FIG. 6 has a total of three connection fittings 114, 114', 114", each surrounded by a chamber bushing 116, 116', 116", respectively, so that a total of three annular chambers are available for introducing tube sheaths of multi-lumen tubes. The central lumens of the tubes can be joined together via bores that penetrate the connection fittings. The radially offset additional lumens can be joined via corresponding channels in the basic body 110. Each connection fitting of the embodiment of the invention shown in FIG. 6 is assigned clamping tongues 130, 130', 130" and clamping bushings 160, 160', 160" of the type shown in FIGS. 2 through 4. One of the connection fittings 160" of the connection device shown in FIG. 6 is embodied as shorter than the other two connection fittings 160, 160'. That connection fitting serves for instance to join a multi-lumen tube to the vacuum therapy apparatus. The connection can be more easily released than that of the other multi-lumen tubes thrust onto the other connection fittings, since in these other tubes the connection fittings forms an abutment for the clamping tongues, so that the clamping force can be reinforced. Thus a "rated breaking point" can be furnished in the vicinity of this connection fitting.

The invention is not limited to the embodiments of the invention explained in conjunction with the drawings. Connection devices according to the invention can also be used by directly connecting a multi-lumen tube to a vacuum therapy apparatus. Moreover, they can be used for connecting four or more multi-lumen tubes. An arbitrary number of additional lumens, which are joined together via distributor chambers, can be used.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A connection device for a multi-lumen line, the connection device comprising:
   a central collar defining a distributor chamber;
   at least one connection fitting extending from the central collar designed for tight and releasable connection to the multi-lumen line;
   wherein when the multi-lumen line is connected to the connection device, at least one lumen line of the multi-lumen line opens into the distributor chamber and the distributor chamber is sealed off in a fluid-tight fashion from at least one other line lumen, such that fluid exchange between the distributor chamber and the at least one other line lumen is prevented; and wherein the central collar and connection fitting are a one-piece basic body designed for connection of at least two multi-lumen lines; and wherein the basic body additionally furnishes at least one channel for removing a fluid from or introducing a fluid to the distributor chamber, and wherein the basic body furnishes two or more of the distributor chambers, of which at least two are connected with each other via at least one of the channels.

2. The device of claim 1, further comprising at least one chamber bushing extending coaxially from the central collar and spaced apart from the connection fitting to form an annular gap between the connection fitting and the chamber bushing; and further comprising a securing device that is adjustable between a release position, which enables the introduction of the multi-lumen line into the annular gap, and a securing position, which secures the multi-lumen line within the connection device.

3. The device of claim 2 wherein the securing device comprises a clamping bushing extending coaxially to the chamber bushing.

4. The device of claim 3 further comprising at least two clamping tongues extending from the chamber bushing, wherein the clamping tongues are offset radially inward when the clamping bushing is moved from the release position to the securing position.

5. The device of claim 2 further comprising a stop that limits the introduction of the line into the annular gap.

6. The device of claim 5 wherein the stop is a radial shoulder on the connection fitting.

7. The device of claim 5 further comprising a window in the central collar through which visual monitoring of the contact of a line end with the stop is enabled.

8. The device of claim 2 further comprising a sealing device in the annular gap.

9. The device of claim 8 wherein the sealing device is a sealing shell received in the annular gap, the sealing shell having at least one sealing lamella surrounding the chamber bushing axis and coming into contact with the outer boundary face of the line when it is introduced.

10. The device of claim 9 wherein the sealing shell further comprises an encompassing bead and the chamber bushing further comprises a radially inner indention, wherein a ring snap connection is formed between the sealing shell and the chamber bushing.

11. The device of claim 10 wherein the encompassing bead has at least one opening whereby the encompassing bead does not completely surround the sealing shell.

12. The device of claim 8, wherein the sealing device comprises a polygonal lamella seal.

13. The device of claim 8, wherein the sealing device comprises a round lamella.

14. The device of claim 8, wherein the sealing device is a face-end seal.

15. The device of claim 8, wherein the sealing device is an o-ring.

16. The device of claim 8, wherein the sealing device is a radial shaft seal.

17. The connection device of claim 2, wherein the central collar and connection fitting are a one-piece basic body designed for connection of at least two multi-lumen lines; and wherein the basic body additionally furnishes at least one channel for removing a fluid from or introducing a fluid to the distributor chamber.

18. The device of claim 17 wherein the basic body furnishes two or more of the distributor chambers, of which at least two are connected with each other via at least one of the channels.

19. A connection device for a multi-lumen line, the connection device comprising:

a central collar defining a distributor chamber;

at least one connection fitting extending from the central collar designed for tight and releasable connection to the multi-lumen line;

wherein when the multi-lumen line is connected to the connection device, at least one lumen line of the multi-lumen line opens into the distributor chamber and the distributor chamber is sealed off in a fluid-tight fashion from at least one other line lumen, such that fluid exchange between the distributor chamber and the at least one other line lumen is prevented;

at least one chamber bushing extending coaxially from the central collar and spaced apart from the connection fitting to form an annular gap between the connection fitting and the chamber bushing; and further comprising a securing device that is adjustable between a release position, which enables the introduction of the multi-lumen line into the annular gap, and a securing position, which secures the multi-lumen line with the connection device;

a stop that limits the introduction of the line into the annular gap; and a window in the central collar through which visual monitoring of the contact of a line end with the stop is enabled.

20. A connection device for a multi-lumen line, the connection device comprising:

a central collar defining a distributor chamber;

at least one connection fitting extending from the central collar designed for tight and releasable connection to the multi-lumen line;

wherein when the multi-lumen line is connected to the connection device, at least one lumen line of the multi-lumen line opens into the distributor chamber and the distributor chamber is sealed off in a fluid-tight fashion from at least one other line lumen, such that fluid exchange between the distributor chamber and the at least one other line lumen is prevented;

at least one chamber bushing extending coaxially from the central collar and spaced apart from the connection fitting to form an annular gap between the connection fitting and the chamber bushing; and further comprising a securing device that is adjustable between a release position, which enables the introduction of the multi-lumen line into the annular gap, and a securing position, which secures the multi-lumen line within the connection device;

a sealing device in the annular gap, wherein the sealing device is a sealing shell received in the annular gap, the sealing shell having at least one sealing lamella surrounding the chamber bushing axis and coming into contact with the outer boundary face of the line when it is introduced;

wherein the sealing shell further comprises an encompassing bead and the chamber bushing further comprises a radially inner indention, wherein a ring snap connection is formed between the sealing shell and the chamber bushing.

* * * * *